(12) United States Patent
Cobb et al.

(10) Patent No.: US 6,241,981 B1
(45) Date of Patent: Jun. 5, 2001

(54) COMPOSITION AND METHOD FOR REPAIRING NEUROLOGICAL TISSUE

(75) Inventors: Mark A. Cobb, Newburgh; Stephen F. Badylak, West Lafayette; Gary Isom, West Lafayette; Archana Sharma, West Lafayette, all of IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/242,628

(22) PCT Filed: Sep. 16, 1997

(86) PCT No.: PCT/US97/16294

§ 371 Date: Feb. 19, 1999

§ 102(e) Date: Feb. 19, 1999

(87) PCT Pub. No.: WO98/10775

PCT Pub. Date: Mar. 19, 1998

Related U.S. Application Data
(60) Provisional application No. 60/026,197, filed on Sep. 16, 1996.

(51) Int. Cl.$^7$ .............................. A01N 63/00; A01N 65/00
(52) U.S. Cl. ............................................. 424/93.1; 435/335
(58) Field of Search ..................................... 424/93.1, 335

(56) References Cited

U.S. PATENT DOCUMENTS

| | | |
|---|---|---|
| 4,902,508 | 2/1990 | Badylak et al. . |
| 5,275,826 | 1/1994 | Badylak et al. . |
| 5,281,422 | 1/1994 | Badylak et al. . |
| 5,360,610 | 11/1994 | Tice et al. . |
| 5,514,181 | 5/1996 | Light et al. . |
| 5,695,998 | * 12/1997 | Badylak et al. ..................... 435/391 |

* cited by examiner

*Primary Examiner*—Dwayne C. Jones
(74) *Attorney, Agent, or Firm*—Barnes & Thornburg

(57) ABSTRACT

The present invention relates to tissue graft constructs useful in promoting regrowth and healing of damaged or diseased nuerological related tissue structures. More particularly this invention is directed to a submucosa tissue graft construct and a method of inducing the formation of endogenous neurological structures at a site in need of endogenous neurological related tissue growth.

23 Claims, No Drawings

COMPOSITION AND METHOD FOR REPAIRING NEUROLOGICAL TISSUE

CROSS-REFERENCE TO RELATED APPLICATIONS

This application is a U.S. national application of international application Ser. No. PCT/US97/16294 filed Sep. 16, 1997, which claims priority to U.S. provisional application Ser. No. 60/026,197 filed Sep. 16, 1996.

FIELD OF THE INVENTION

This invention relates to tissue graft constructs useful in promoting regrowth and healing of damaged or diseased neurological related tissue structures. More particularly this invention is directed to a method of inducing the formation of endogenous neurological structures at a site in need of endogenous neurological related tissue growth by contacting the site with a submucosal tissue graft construct.

BACKGROUND AND SUMMARY OF THE INVENTION

The neurosurgeon is frequently confronted with the necessity of repairing dural defects due to trauma, tumor resection, and decompressive procedures. Numerous materials have been investigated for use in the repair of the dura mater and underlying tissues. Current options include autologous materials (e.g. pericranium, temporalis fascia, and tensor fascia lata), lyophilized cadaveric materials (e.g. dura mater and tensor fascia lata) and synthetic materials (e.g. Silastic sheets, Dacron sheets, Vicryl mesh); however, each of these materials is associated with significant limitations.

One object of the present invention is to provide a biodegradable material that can serve as a dural substitute.

Many individuals have suffered injuries to their central nervous system that leave the individual partially paralyzed or result in reduced motor function. Repair strategies and graft material for repairing damage to the central nervous system do not currently exist. In particular nerve fibers within the brain and the spinal cord, which differ structurally from peripheral nerves, will not regenerate after they have been severed or crushed. For example there is no currently known treatment for humans that promotes functional regeneration across a complete spinal cord transection or a severed optic nerve.

An additional object of the present invention is to provide a composition and method that promotes the production of endogenous central nerve cells thus allowing the repair of damage to both central nervous system tissues and peripheral nerve tissues.

It is known that compositions comprising the tunica submucosa delaminated from both the tunica muscularis and at least the luminal portion of the tunica mucosa of the intestine of warm-blooded vertebrates can be used as tissue graft materials. See, for example, U.S. Pat. Nos. 4,902,508 and 5,281,422. The compositions described in those patents are characterized by excellent mechanical properties, including high compliance, a high burst pressure point, and an effective porosity index which allowed such compositions to be used beneficially for vascular graft constructs and in connective tissue replacement applications. When used in such applications the submucosal graft constructs appear to serve as a matrix for the regrowth of the tissues replaced by the graft constructs. Furthermore, as described in U.S. Pat. No. 5,275,826 fluidized forms of vertebrate submucosal tissues can also be used as injectable or implantable tissue grafts without loss of biotropic properties. Significantly, too, in over 600 cross-species implants, submucosa-derived graft compositions have never been shown to elucidate a tissue graft rejection reaction.

Applicants have discovered that submucosal tissue induces the growth and proliferation of neurological related tissues, including the dura mater and nerve cells of the central and peripheral nervous system. Accordingly, the present invention is directed to the use of submucosal tissue as a graft construct for promoting the repair of damaged or diseased neurological related tissues.

DETAILED DESCRIPTION OF THE PREFERRED EMBODIMENTS

The submucosal tissue constructs of the present invention have been found to promote or induce the growth of neurological related tissues. In accordance with the present invention the term neurological related tissues includes neurons and glial cells, and dura mater, arachnoid and pia mater tissues. There is provided in accordance with this invention a method for utilizing compositions comprising warm-blooded vertebrate submucosal tissue to repair or to enhance the repair of damaged or diseased neurological related tissues in a warm-blooded vertebrate. The method comprises the step of contacting the site in need of repair with a composition comprising submucosal tissue.

Submucosal tissue suitable for use in accordance with the present invention comprises natural collagenous matrices that include highly conserved collagens, glycoproteins, proteoglycans, and glycosaminoglycans in their natural configuration and natural concentration. One source of submucosal tissue is the intestinal tissue of a warm-blooded vertebrate. Small intestinal tissue is a preferred source of submucosal tissue for use in this invention.

Submucosal tissue for use in this invention is derived from various warm-blooded vertebrate sources, including intestinal tissue harvested from animals raised for meat production, such as pigs, cattle and sheep or other warm-blooded vertebrates. This tissue can be used in either its natural configuration or in a comminuted or partially enzymatically digested fluidized form. Vertebrate submucosal tissue is a plentiful by-product of commercial meat production operations and is thus a low cost graft material, especially when the submucosal tissue is used in its native layer sheet configuration.

Suitable intestinal submucosal tissue typically comprises the tunica submucosa delaminated from both the tunica muscularis and at least the luminal portion of the tunica mucosa. In one embodiment of the present invention the intestinal submucosal tissue comprises the tunica submucosa and basilar portions of the tunica mucosa including the lamina muscularis mucosa and the stratum compactum. Those layers are known to vary in thickness and in definition dependent on the source vertebrate species.

The preparation of submucosal tissue for use in accordance with this invention is described in U.S. Pat. No. 4,902,508, the disclosure of which is expressly incorporated herein by reference. A segment of vertebrate intestine, preferably harvested from porcine, ovine or bovine species, but not excluding other species, is subjected to abrasion using a longitudinal wiping motion to remove the outer layers, comprising smooth muscle tissues, and the innermost layer, i.e., the luminal portion of the tunica mucosa. The submucosal tissue is rinsed with saline and optionally sterilized; it can be stored in a hydrated or dehydrated state.

Lyophilized or air dried submucosa tissue can be rehydrated and used in accordance with this invention without significant loss of its biotropic and mechanical properties.

Submucosal tissue prepared from warm-blooded vertebrate organs typically has an abluminal and a luminal surface. The luminal surface is the submucosal surface facing the lumen of the organ source and typically adjacent to an inner mucosa layer in the organ source, whereas the abluminal surface is the submucosal surface facing away from the lumen of the organ source and typically in contact with smooth muscle tissue in the organ source.

The submucosal tissue graft compositions of the present invention can be preconditioned by stretching the material in a longitudinal or lateral direction as described in U.S. Pat. No. 5,275,826, the disclosure of which is expressly incorporated herein by reference. Multiple strips/pieces of submucosal tissue can also be fused together to form a unitary multi-layered submucosal tissue construct having a surface area greater than any to the individual strips/pieces of submucosal tissue. The process for forming large area/ multilayered submucosal tissue constructs is described in U.S. patent application Ser. No. 08/418,515, the disclosure of which is expressly incorporated herein by reference. In summary, the process of forming large area sheets of submucosal tissue comprises overlapping at least a portion of one strip of submucosal tissue with at least a portion of another strip of submucosal tissue and applying pressure at least to said overlapped portions under conditions allowing dehydration of the submucosal tissue. Under these conditions the overlapped portions will become "fused" to form a unitary large sheet of tissue.

The large area graft constructs consist essentially of submucosal tissue, free of potentially compromising adhesives and chemical pretreatments, and they have a greater surface area and greater mechanical strength than the individual strips used to form the graft construct. The multilayered submucosal constructs can optionally be perforated as described in U.S. patent application Ser. No. 08/418,515, the disclosure of which is expressly incorporated herein by reference. The perforations of the submucosal tissue construct allow extracellular fluids to pass through the tissue graft material, decreasing fluid retention within the graft and enhancing the remodeling properties of the tissue grafts. The perforation of the submucosal tissue is especially beneficial for multi-laminate tissue graft constructs wherein the perforations also enhance the adhesive force between adjacent layers.

The submucosal tissue specified for use in accordance with this invention can also be in a fluidized form. Submucosal tissue can be fluidized by comminuting the tissue and optionally subjecting it to enzymatic digestion to form a substantially homogenous solution. The preparation of fluidized forms of submucosa tissue is described in U.S. Pat. No. 5,275,826, the disclosure of which is expressly incorporated herein by reference. Fluidized forms of submucosal tissue are prepared by comminuting submucosa tissue by tearing, cutting, grinding, or shearing the harvested submucosal tissue. Thus pieces of submucosal tissue can be comminuted by shearing in a high speed blender, or by grinding the submucosa in a frozen or freeze-dried state to produce a powder that can thereafter be hydrated with water or a buffered saline solution to form a submucosal fluid of liquid, gel-like or paste-like consistency. The fluidized submucosa formulation can further be treated with enzymes such as protease, including trypsin or pepsin at an acidic pH, for a period of time sufficient to solubilize all or a major portion of the submucosal tissue components and optionally filtered to provide a homogenous solution of partially solubilized submucosa.

The graft compositions of the present invention can be sterilized using conventional disinfection/sterilization techniques including glutaraldehyde tanning, formaldehyde tanning at acidic pH, propylene oxide treatment, ethylene oxide treatment, gas plasma sterilization, gamma radiation or electron beam treatment, and peracetic acid (PAA) disinfection. Sterilization techniques which do not adversely affect the mechanical strength, structure, and biotropic properties of the submucosal tissue are preferred. For instance, strong gamma radiation may cause loss of strength of the sheets of submucosal tissue. Preferred sterilization techniques include exposing the graft to peracetic acid, 1–4 Mrads gamma irradiation (more preferably 1–2.5 Mrads of gamma irradiation) or gas plasma sterilization. Typically, the submucosal tissue is subjected to two or more sterilization processes. After the submucosal tissue is treated in an initial disinfection step, for example by treatment with peracetic acid, the tissue may be wrapped in a plastic or foil wrap and sterilized again using electron beam or gamma irradiation sterilization techniques.

In accordance with one embodiment submucosal tissue is used as a tissue graft construct for the replacement or repair of damaged or diseased neurological related tissues. In particular the present submucosal tissue constructs have been found to promote the growth and proliferation of neurons. Accordingly, the present compositions can be used in a method of repairing damaged or diseased neurological related tissues in a warm-blooded vertebrate.

The submucosal tissue construct used in accordance with the present invention comprises intestinal submucosal tissue delaminated from both the tunica muscularis and at least the luminal portion of the tunica mucosa of warm-blooded vertebrate intestine, or a digest thereof. The construct can be combined with an added growth factor such as vascular endothelial growth factor, nerve growth factor or fibroblast growth factor or growth factor containing extracts of submucosal tissue. Alternatively, the tissue graft construct can comprise submucosal tissue in combination with peripheral neuronal tissue and optionally added growth factors.

In one embodiment, solid forms of submucosal tissue are combined with one or more growth factors by soaking the tissue in a buffered solution containing the growth factor. For example the submucosal tissue is soaked for 7–14 days at 4° C. in a PBS buffered solution containing about 5 to about 500 mg/ml, or more preferably 25 to about 100 mg/ml of the growth factor. Submucosal tissue readily bonds to proteins and will retain an association with a bioactive agent for several days. However, to enhance the uptake of the growth factors into the submucosal tissue, the tissue can be partially dehydrated before contacting the growth factor solution. For compositions comprising fluidized, solubilized or guanidine extracts of submucosal tissue, lyophilized powder or solutions of growth factors can be directly mixed with the submucosal tissue. For example, fluidized or solubilized submucosal tissue can be mixed with a growth factor and then packed within a tube of submucosal tissue (or other biodegradable tissue). The open end of the tube is sealed shut after filling the tube with the fluidized or solubilized submucosal tissue.

In accordance with the present invention, submucosal tissue of a warm-blooded vertebrate is used to manufacture a tissue graft construct useful for inducing the repair of neurological tissue in a warm-blooded vertebrate. The manufacture comprises the steps of combining submucosal tissue of a warm-blooded vertebrate, or a digest thereof, with an added growth factor selected from the group consisting of vascular endothelial growth factor, nerve growth factor and fibroblast growth factor.

In one embodiment the submucosal tissue is used to manufacture a graft construct that directs the in vivo growth of neurons along a predetermined path. The manufacture comprises the steps of forming a tube of biodegradable material, and filling the tube with fluidized submucosal tissue. The tube should be formed to have a diameter about 0.5 mm to about 4 mm for peripheral nerve applications, and about 1 mm to about 2 cm for central nerve applications. In one embodiment the tube is formed from submucosal tissue wherein the submucosal tissue is manipulated to define a cylinder having a diameter of the preferred size. Typically the submucosal tissue is prepared directly from intestinal tissue and thus has a generally cylindrical shape. The tissue can be manipulated to define a cylinder having the preferred diameter by suturing or otherwise securing the graft longitudinally and removing the excess tissue. For example, the graft construct can be prepared by selecting a sterile glass rod having an outer diameter equal to the desired diameter of the lumen of the formed graft construct. The glass rod is introduced into the graft lumen, redundant tissues is then gathered, and the desired lumen diameter is achieved by suturing along the length of the graft or by using other art recognized tissue securing techniques.

Alternatively, a tube of submucosal tissue can be formed by wrapping strips of submucosal tissue onto a mandrel wherein the wrapped submucosal tissue is overlapped leaving no portion of the underlying mandrel exposed. See U.S. Provisional Application Ser. No. 60/032,679, the disclosure of which is expressly incorporated herein. The submucosal tissue can be spirally wrapped onto a mandrel as a continuous piece of submucosal tissue, and multiple strips of submucosal tissue can be used to form the tubular constructs. The wrapped submucosal tissue is then compressed under dehydrating conditions and the tubular prosthesis is removed from the mandrel. The amount of overlap in a spirally wrapped construct in accordance with this embodiment ranges between 10 to 60% of the width of the previous strip and more preferably the overlapped portion is a 50% overlap.

Upon formation of the biodegradable tube, the tube is filled with fluidized or solubilized submucosal tissue and the tube is sealed at one or both ends of the tube using art recognized methods (including clamping, suturing, binding pastes, and compression under dehydrating conditions). Alternatively the tube can be sealed at one or both ends of the tube before being filled with fluidized/solubilized tissue. The tube can then be filled by injecting fluidized/solubilized tissue into the lumen through the use of a syringe.

The submucosal tissue graft constructs of the present invention are used to repair neurological related tissues and more particularly components of the central and peripheral nervous system. The method comprises contacting the site in need of repair with a composition comprising intestinal submucosal tissue delaminated from both the tunica muscularis and at least the luminal portion of the tunica mucosa of warm-blooded vertebrate intestine. The submucosal tissue can be used, for example, in sheet, strip, braid or loop form and surgically implanted at the site in need of repair. The submucosal tissue composition can also be administered in a fluidized form and injected into the warm-blooded vertebrate at the site in need of repair. Finally the composition may comprise fluidized submucosal tissue filled cylinder of submucosal tissue.

In one embodiment in accordance with the present invention, the submucosal tissue constructs are used to induce the formation of neurological related tissue between endogenous neurological tissue structures in a warm blooded vertebrate. The method comprises the steps of surgically implanting a tissue graft composition comprising submucosal tissue of a warm-blooded vertebrate, into the host to bridge the endogenous neurological tissue structures and induce endogenous neurological related tissue growth between the bridged neurological structures.

When submucosal tissue comprising the tunica submucosa and basilar portions of the tunica mucosa including the lamina muscularis mucosa and the stratum compactum, is used in non-fluidized form, it is preferred that it be implanted so that the stratum compactum contacts the surface tissues most prone to forming adhesions with the graft material.

In accordance with one embodiment damage to the spinal cord can be repaired by manually separating adjacent longitudinal neural fibers in the spinal cord, wherein the separations or incisions run parallel to the axons of the neurons of the spinal column and penetrate through the dura mater, arachnoid and pia mater layers. Strips of submucosal tissue are surgically implanted into the vertical separations or in natural sulci and thus are in direct contact with neurological related tissues and are held in place by those tissues. Alternatively, sheets of submucosa tissue can be used to wrap the exterior of the damaged area to promote repair of the damaged tissues. Optionally sutures can be utilized to secure the submucosal tissue in its desired location.

In applications where the spinal cord has been transected, the submucosal tissue can be positioned between the two severed ends to bridge the gap and serve as a framework that directs the growth of neurons of the two severed ends towards one another. Fluidized forms of submucosa can also be used in accordance with the present invention to repair damaged or diseased neurological related tissues. Advantageously the fluidized forms can be injected into the site in need of repair and thus can be used in a less invasive procedure to induce the proliferation of endogenous neurological related tissues.

In accordance with one embodiment a tissue graft composition, comprising submucosal tissue of a warm-blooded vertebrate, is administered to a warm-blooded vertebrate at a site in need of endogenous neurological related tissue growth in an amount effective to induce endogenous neurological related tissue growth at the site the composition is administered. The biotropic properties of submucosal tissue promote the growth of neurological tissue along "tracts" as defined by the path of the implanted submucosal tissue. Accordingly the growth of neurons, including neurons of central and peripheral nervous system, can be directed to a site in need of innervation. In one embodiment the growth of neurological tissue is "directed" through the use of a tissue graft construct comprising a tube filled with fluidized submucosal tissue. In this embodiment healthy neuronal tissue is inserted into one end of the tube and is placed in direct contact with the fluidized submucosal tissue contained within the tube. The opposite end of the tube is then placed at or near the site in need of innervation. The tube is fixed in place and provides an in vivo conduit for new neuronal growth and innervation of the desired site. The tube of fluidized submucosal tissue can also be utilized to repair transected nerves, wherein the two ends of the transected nerve are inserted into the tube to induce reattachment of the severed ends and restore nerve function.

Each of the following methods can be used in conjunction with the tissue graft constructs of the present invention to provide a conduit for directed de novo growth of neuronal tissues. In one embodiment submucosal tissue is prepared in the shape of a tube having a lumen and two open ends. In one embodiment, the tube of submucosal tissue is directly implanted into the host organism and the end of a damaged nerve fiber can be inserted into the lumen of the submucosal tissue tube. A syringe is then used to fill the tube with comminuted or solubilized submucosal tissue. Alternatively, submucosal tissue can be formed in the shape of a tube, filled with fluidized/solubilized submucosal tissue and sealed at each end. The sealed tube of submucosal tissue can then be stored until needed. In one embodiment the sealed tube of submucosal tissue is inserted into the host organism and fixed in place using techniques known to those skilled in the art. The inserted graft construct provides a conduit for new neuronal tissue growth. In one preferred embodiment, a slit or hole is cut into the tube of submucosal tissue and a damaged or resected end of a nerve tissue is inserted through the slit or hole and into the lumen of the tube.

The submucosal tissue used in accordance with the present invention can be used alone or combined with added growth factors such as vascular endothelial growth factor, nerve growth factor or acidic fibroblast growth factor. In addition peripheral nerve implants can be used in combination with submucosal tissue to enhance the repair of neuronal tissues. The term peripheral nerve implant as used herein refers to neuronal tissue harvested from the peripheral nervous system of a warm blooded vertebrate, and preferably autologous peripheral neuronal tissue. Additional components can be added to the neuronal tissue graft compositions that provide the compositions with structural support for applications involving the spinal cord, especially where portions of the spinal column are missing or need to be replaced. For example hydroxyapatite and/or other biocompatible calcium containing minerals can be combined with the graft composition, or metal posts or wires can also be used in combination with the submucosal tissue to give additional structural support for the replacement tissue.

The submucosal tissue graft constructs of the present invention can also be utilized to promote the growth and proliferation of other central nervous-associated and support tissues. Submucosal tissue enhances the repair of glial cells, and dura mater, arachnoid and pia mater tissues.

In one embodiment the submucosal tissue is used as a dural substitute, formed as a patch tissue graft shaped to cover a defect or hole formed in the endogenous dura mater. Presently available options for dura mater substitute materials have significant limitations: autologous materials are frequently inadequate in quantity and are obtained with the associated morbidity of additional incisions, and the handling characteristics of synthetic sheets are poor compared to biological materials. In addition, concern has been raised regarding long term risks of hemorrhage from tissue reaction to synthetic graft materials. Cadaveric dura is expensive, occasionally limited in supply, and has only fair handling characteristics. Of greater concern is its documented role as a vector in the transmission of the slow viruses such as Jakob-Creutzfeldt disease.

Submucosal tissue provides an excellent dural substitute since this material does not invoke an adverse immunologic response and induces proliferation of endogenous cells which invade and ultimately replace the graft with endogenous cells. An experiment was conducted utilizing rat hosts to confirm the utility of submucosal tissue compositions as dural substitutes.

As described in Example 1, submucosal tissue implanted in a rat following dural resection functions as a suitable dural substitute. At 28 days after implantation remodeling of the submucosal tissue has begun, as is indicated by the presence of spindle cells, aggressive neovascularization, and eosinophilic staining of the connective tissue matrix. The incorporation and remodeling of the graft takes place in the absence of any adverse effects on the underlying cerebral cortex.

EXAMPLE 1

Submucosal Tissue as a Dural Substitute
Experimental Design and Surgical Procedure Twenty medium size Sprague-Dawley laboratory rats were anesthetized (ketamine 90 mg/kg and xylazine 10 mg/kg, IM) and placed in a stereotaxic head frame to stabilize the cranium. The scalp was shaved, prepped with chlorhexadine, and infiltrated with 1% lidocaine. Following incision of the fascia at the superior temporal line, the temporalis muscles were elevated laterally through a midline scalp incision, exposing the parietal convexities. Bihemispheric parietal craniectomies, approximately 4 mm×8 mm, were made with an electric hand drill and burr. The dura, a thin, nearly transparent membrane in the rat, was resected at the craniectomy sites under loop magnification. Care was taken not to injure the underlying cerebral cortex.

Small intestinal submucosa graft material, in sheet form, was prepared in accordance with the present invention and sterilized by exposure to 0.1% peracetic acid. The graft was cut to the appropriate size and placed as an onlay graft over one convexity, with the graft orientated so that the stratum compactum surface faced the cerebral cortex. The contralateral hemisphere received no graft, thus serving as a control for host response to the operative procedure. In two animals the bone fragment was replaced. The wound was irrigated with normal saline and closed with staples. A single post operative dose of ampicillin (25 mg/kg, SQ) was given. Immediate post operative care included placement on a heating pad, covering with a towel, turning every 15 minutes until awake and moving, and monitoring heart rate and respirations. The animals were monitored daily for the occurrence of seizures or neurological deficits, appetite and fluid intake, and weight.

Ten of the rats were sacrificed by barbiturate overdose (150 mg/kg, IC) 7 days after graft placement. The remaining ten rats were sacrificed 28 days after graft placement.
Histological Preparation and Evaluation Three of the twenty rats died of anesthetic related complications in the early post operative period. The remaining seventeen rats recovered uneventfully from the procedure without evidence of seizures, infection, or neurologic deficit. Eight rats were sacrificed at day 7. Nine were sacrificed at day 28.

Following sacrifice, the rats were perfused with formalin via carotid artery catheters. The cranium was then fixed in formalin and decalcified. Six micron thick sections were cut, stained with hematoxylin and eosin, and prepared for histologic examination. The tissues examined included the interfaces of the graft with the cortex, bone, and scalp. The control side was similarly prepared.

Microscopic evaluation of the specimens was augmented with quantification of the cellular infiltrate, vascularity, and thickness of the defect site using an image analysis system (Optimus Image Analysis System; Bioscan, Inc; Edmonds, Wash.). Data for the submucosal graft implant treated defect site were compared to the control site at both the 7 day and 28 day time points. The numerical scores given to the remodeling tissues were based upon the criteria given in Table 1. The values were compared using the Student's T test. The total score for the respective groups was used to test the null hypothesis that there was no difference between the morphologic changes seen in the submucosa filled versus the non-submucosa filled defect sites at either 7 or 28 days. A p-value less than 0.05 was considered significant.

TABLE 1

Quantitative Histological Assessment of Submucosa Dural Onlay Grafting vs. Control

| Group | Thickness | Vascularity | Cellular Density | Total Score |
|---|---|---|---|---|
| 7 day Graft (n = 8) | 1.1 ± 0.2 | 0.9 ± 0.2 | 1.4 ± 0.2 | 3.4 ± 0.8[a] |
| 7 day Control (n = 8) | 0.2 ± 0.1 | 0.1 ± 0.1 | 0.1 ± 0.1 | 0.4 ± 0.1 |
| 28 day Graft (n = 9) | 1.9 ± 0.3 | 1.9 ± 0.4 | 0.8 ± 0.3 | 4.6 ± 1.1[a] |
| 28 day Control (n = 9) | 1.1 ± 0.3 | 0.8 ± 0.2 | 0.3 ± 0.2 | 2.2 ± 0.5 |

[a]value is significantly different from the value in the control group at a p-value of <0.05

The submucosa graft sites are compared with the control sites using thickness, vascularity, and cellular density as the scoring criteria. The values listed represent the mean value ±S.E.M.

| Criteria | Score | Description of Score |
|---|---|---|
| Thickness | | |
| 0 = | | <100 $\mu M$ |
| 1 = | | 100–200 $\mu M$ |
| 2 = | | >200 $\mu M$ |
| Vascularity | | |
| 0 = | | 0–1 vessel cross sections / 100, $\mu M^2$ |
| 1 = | | 2–4 vessel cross sections / 100 $\mu M^2$ |
| 2 = | | $\geq$5 vessel cross sections / 100 $\mu M^2$ |
| Cellular density | | |
| 0 = | | Total cell area: extracellular matrix material <0.5 |
| 1 = | | Total cell area: extracellular matrix material 0.5–1.0 |
| 2 = | | Total cell area: extracellular matrix material >1.0 |

Histologic evaluation showed graft infiltration by spindle shaped mononuclear cells, deposition of connective tissue, and neovascularity. Furthermore, histological analysis revealed distinct differences between the defects repaired with submucosa tissue versus the control (i.e. defects left to heal without any material placed at the defect site). The total score for the respective groups were compared using the Student's T test, significance being accepted for a p value <0.05. A significant difference between the histologic scores of the submucosa graft site and control site was found at 7 days (3.4±0.8 vs. 0.1±0.1) and at 28 days (4.6±1.1 vs. 2.2±0.5). No evidence of adverse effect on the underlying cortex was observed.

At day 7, the main differences between the two groups were the cellular infiltrate, vascularity, and the thickness of the connective tissue deposited at the defect site. These morphologic changes were compared in a semiquantitative fashion as defined in Table 1. This method of comparison showed increased thickness, increased vascularity, and greater cellular infiltration of the submucosa treated defects versus the non submucosa treated control defects. The mononuclear cells which were seen within and around the submucosa material at day 7 often showed a spindle shape and were surrounded by eosinophilic staining extracellular matrix (ECM) material. The remodeling submucosa material showed a large number of capillary sized blood vessels in contrast to those observed in the non-submucosa control defects.

By 28 days, the cellular infiltrate had moderated in the submucosa-filled defects and the amount of ECM had increased. The eosinophilic staining connective tissue in and around the submucosa showed orientation in the direction that would extend from one edge of the cut calvaria to the opposite edge. There was also moderate organization of the connective tissue seen in the non-submucosa defects; however the amount of material present was much less than the submucosa defect sites. The submucosa material itself was not discernible by day 28. The ECM appeared homogeneous in these H&E stained sections. The cellular infiltrate was much less at day 28 than at day 7 and virtually all of the cells present were consistent with spindle shaped mesenchymal cells.

Occasional adhesions were noted between the ECM within the defect site and the underlying cerebral cortex in both the submucosa and non-submucosa sides. None of the specimens showed changes consistent with encephalitis, degeneration, or necrosis.

EXAMPLE 2

Submucosal Tissue as a Dural Substitute in the Canine Model

Experimental Design and Surgical Procedure

Eight medium size mongrel dogs (20–30 kg) were anesthetized, intubated, and placed in the sternal supine position (induction with 2% thiopental 1.0 mg/kg, intravenous; maintenance with isoflurane 1%–2%; atropine 0.5 mg/ml, intravenous). Ophthalmic ointment was administered. The scalp was shaved, prepped with chlorhexadine, and infiltrated with 1% lidocaine. Through a midline scalp incision and following incision of the fascia at the superior temporal line, the temporalis muscle was elevated laterally exposing the parietal convexity. A 2×3 cm temporoparietal craniotomy was made with an electric hand drill and burr. Bleeding bone edges were waxed. The dura was resected at the craniotomy sites under loop magnification. Care was taken to avoid injury to the underlying cerebral cortex.

The submucosal tissue graft material was harvested and sterilized by exposure to 0.1% peracetic acid in 20% ethanol for 120 minutes. The material was cut to the appropriate size and placed with the compacted basal layers of the tunica mucosa toward the cerebral cortex and secured with braided nylon suture. In five animals, a contralateral procedure was performed in which the resected autologous dura was used to close the defect, thus serving as a control for host response to the operative procedure.

In three animals, the contralateral side was subjected to dural resection with intestinal submucosal replacement sixty days after the initial procedure. The craniotomy flap was replaced, the wound irrigated with normal saline, and closed with staples. Tribiotic ointment, sterile head dressing, and an Elizabethan collar were applied. Antibiotic treatment consisting of cephalexin 1000 mg, PO, b.i.d., one day preoperatively and for three days postoperatively was administered. Immediate post operative care included covering with a blanket and monitoring heart rate and aspirations. Post operative pain was treated with butorphanol (2.4 mg, intramuscular) and Ace Promazine (2.0 mg, intramuscular). The animals were monitored for the occurrence of seizures or neurological deficits, appetite and fluid intake, and weight. Sacrifice was by barbiturate overdose (150 mg/kg, intracardiac) on 7, 30, 60, 90, and 120 days after initial graft placement and 7, 30, and 60 days following repeat intestinal submucosal tissue exposure. Preceding sacrifice 5 cc of CSF was aspirated via suboccipital puncture and examined for different cell count.

Histological Preparation and Evaluation

Following sacrifice, the head and neck of the dogs were perfused with formalin via carotid artery catheters. The cranium was then fixed in formalin and decalcified. Following embedding in paraffin, six micron thick sections of the surgical sites were cut, stained with hematoxylin and eosin, and prepared for histologic examination. The tissues examined included the interfaces of the graft with the cerebral cortex, bone, and scalp.

Results

All eight dogs recovered uneventfully from the procedure without evidence of seizures, infection, or neurologic deficit. Repeat grafting was not accompanied by clinical evidence of sensitization to the submucosal tissue.

At day 7 following implantation, an intense mononuclear cell response into the intestinal submucosal tissue was present, with extensive neovascularization and deposition of disorganized extracellular matrix around the submucosal tissue. However, there was no evidence for involvement of the underlying cerebral cortex. There was a small number of spindle shaped cells consistent with fibroblasts around and within the graft site.

At every examination time following the 7 day time period (30, 60, 90, and 120 days) a well organized eosinophilic staining dense connective tissue was evident, with no evidence of the submucosal tissue remaining by day 60. No meningocerebral adhesions were seen. In the dogs subjected to a second exposure to intestinal submucosal tissue, a response indistinguishable from those with single intestinal submucosal tissue exposure was found.

In some animals, in both the test site and the control site, there was a mild inflammatory reaction of the pia mater adjacent to the cerebral. Since this was present in both the control site and the test site it likely represents a response to the surgical procedure. In no animal was there evidence for involvement of the cerebral cortex itself. Neovascularization was more intense at the 7 and 30 day time points in the submucosal tissue sites compared to the control sites. There was no evidence for an immune mediated graft reaction of host sensitization in either the initial implants or in the reimplanted animals. There were no abnormalities in the serum chemistry or CSF cytology found in any of the post operative samples.

Discussion

Current options for a dural substitute include autologous materials (e.g. pericranium, temporalis fascia and tensor fascia lata), lyophilized cadaveric materials (e.g. dura mater and tensor fascia lata), xenogeneic biomaterials (bovine and ovine pericardium) bovine dura, and reconstituted bovine collagen sponge) and synthetic materials (e.g. expanded polymer fluorethylene, Silastic sheets, Dacron sheets, Vicryl mesh). However, each of these materials is associated with significant limitations.

Autologous materials are frequently inadequate in quantity and are obtained with the associated morbidity of additional incisions. The handling characteristics of synthetic sheets are poor compared to biological materials. In addition, concern has been raised regarding long term risks of hemorrhage from tissue reaction adjacent to the graft. Cadaveric dura is expensive, occasionally limited in supply, and has only fair handling characteristics. Its documented role as a vector in the transmission of Jakob-Creutzfeldt disease severely limits its appeal. Likewise, recent evidence of transmission to humans of bovine spongiform encephalopathy raises concern over bovine based neurological tissues.

The dura mater consists primarily of Type I collagen, and thus collagen-based products are reasonable candidates for dural substitution. Furthermore, although relative biological inertness had previously been considered a desirable implant characteristic, there is increasing awareness of the potential advantages of an induced favorable biologic response to grafting. Indeed, fibroblasts and endothelial cells have been shown to invade along a reconstituted collagen scaffolding, replacing it by newly synthesized collagen. Several collagen based preparations have been investigated and appear to exhibit many of these characteristics. Preparations reported for dural substitution include processed porcine peritoneum and dermis, bovine corium and pericardium, ovine pericardium, and multiple reconstituted products of human placenta. Graft incorporation with subsequent resorption is reported for each of these materials. In addition, they produced neither acute immune reactions nor epileptogenic meningoencephalitic scars when applied to cortex.

Nevertheless, only bovine pericardium is commercially available. Thus, a non-bovine based collagen preparation with favorable biological properties appears to offer many benefits while avoiding many disadvantages. The acellular submucosal material of the present invention provides a novel material for dura mater substitute constructs. In addition to the absence of an adverse immunologic response, there is demonstrated a distinctive remodeling of the submucosal tissue and incorporation into the host tissue. The final form of the remodeled dural graft appears to be histologically indistinguishable from native tissue. In addition, exposure to the intestinal submucosal tissue two months following initial grafting was not accompanied by adverse clinical events. Routine CSF cytology provided no evidence for adverse host response to the submucosal tissue graft.

EXAMPLE 3

In vitro Growth and Differentiation of Neuronal Cells Cultured on Submucosal Tissue Pheochromocytoma cells (PC12 cells) are neuronal cells which grow as spherical chromaffin cells in the absence of nerve growth factor (NGF) but differentiate to form sympathetic-like neurons upon exposure to nerve growth factor treatment. PC12 cells are an established and well studied cell line that has been utilized as a model system to study neuronal differentiation and proliferation. The response of PC12 cells to exposure to various forms of submucosa tissue (dehydrated, ETO, PAA) was investigated to determine if submucosal tissue would promote the differentiation, growth and proliferation of neuronal cells.

Cell Culture

Rat Pheochromocytoma (PC12) cells were obtained from American Type Culture Collection (Rockville, Md.) and were cultured as described by Green Tishler (1983). Initially the cells were grown to confluence in monolayers attached to plastic 75 cm flasks. PC12 cells were maintained in RPMI 1640 medium supplemented with 10% horse serum, 5% fetal bovine serum, 1% L-glutamine and 100 units/ml penicillin and 100 ug/ml streptomycin. Cells were seeded in plastic 6 well culture dishes precoated with 0.2 mg/m collagen. PC12 cells, serving as a positive control, were differentiated into sympathoblast-like cells by treatment with nerve growth factor (NGF) at a concentration 50 mg/ml for 7–10 days in RPMI. The medium containing NGF was changed every other day during this period. After 10 days in culture PC12 cells were terminally differentiated and dependent upon NGF for survival.

Chemicals

Horse serum and Bovine serum were purchased from Hyclone (Logan, Utah). RPMI from Gibco BRL (Grand Island, N.Y). Small intestine submucosa was prepared in accordance with the procedures described in the present specification. All other chemicals were purchased from Sigma Chemical Company.

Growth and Differentiation Studies

To demonstrate PC12 cells differentiate on submucosa, cells were seeded (50,000/ml) in plastic uncoated 6 well culture plates, each well containing a 1–2 inches square of submucosa (dehydrated submucosa was preserved as sterile sheet, ETO, PAA) and RPMI media for 10 days. The submucosa was cut in small pieces and placed in cell culture plate wells by sterile forceps and the cells were pipetted onto the submucosa. Cells were observed under a inverted light microscope every day for the changes in PC12 cells.

Every 2, 4, 6, 8 and 10 days pictures were taken to compare the degree of differentiation of PC12 cells by observing quantitatively the number of neurites and neurite length. Each experiment was repeated three times (n=3) in triplicates. Differentiation of the cells was observed for cells in direct contact with the submucosa tissue as well as for cells that were not in direct contact with the submucosa tissue present in the well.

The following controls were used to compare the experimental observations, each control (comprising four wells) was repeated three times (n=3):

Positive Control: Cells were seeded in plastic 6 well culture plates precoated with 0.2 mg/ml collagen and in media containing 50 mg/mi NGF. Cells were grown for 10 days in RPMI containing NGF which was changed every two days.

Negative Control 1: Cells were seeded in plastic 6 well culture plates precoated with 0.2 mg/ml collagen in media containing no NGF.

Negative Control 2: In a second negative control cells were seeded in uncoated plastic 6 well culture plates in the media containing no NGF. Since the cells in negative control 2 started dying and floating after 2–3 days, this control was discarded and no experimental data was compared to this control.

Results

PC12 neuronal cells cultured on submucosal tissue substrates in the absence of any added growth factors differentiate, proliferate and appeared to migrate on the substrate. A time-based study was conducted and observations were taken after 2, 4, 6, 8 and 10 days of culturing in order to correlate time of exposure to the submucosa substrate with changes in neuronal cell differentiation. PC12 cells differentiated on the submucosa substrate as early as one day after seeding. By the second day there was noticeable differentiation as compared to negative control. However, a greater number of cells differentiated and a greater degree of differentiation was observed in the cells after two days of culturing. The qualitative differences between the controls and experimental cells continued after four days of culturing: by day four the positive control showed a greater degree of differentiation than the cells growing on submucosa and finally the negative control showed the least degree of differentiation.

After six days of culture, a visual comparison of the cells under the microscope indicated there was an increase in number of cells. However many cells were floating and clumping. This result is very typical of PC12 in vitro cell cultures, and suggests that those cells that did not differentiate, continued to proliferate and as a result of higher number of cells they clumped. Cells cultured on submucosa by the sixth day had none to very small neurites as compared to positive control, and many cells at this stage appear to migrate on the submucosa. A higher degree of differentiation was observed in cells not in direct contact with the submucosa in the culture plate. That is, those PC12 cells immediately adjacent to, but not in direct contact with, the intestinal submucosal tissue showed good differentiation.

Histological Studies

Time-based histological analysis was utilized to investigate when cells migration occurs on the submucosa substrate and whether or not the migrating cells remain differentiated or change to undifferentiated cells and lose neurites. Wells with submucosa material were flushed with PBS (2 ml) and then subsequently fixed in saline buffered formalin (4 ml) overnight before they could be further processed for slide preparation. Samples in duplicates on days 2, 4, 6, 8 and 10 days of time based studies were provided for slide preparation. Slides are under preparation.

Experiments were also conducted to demonstrate which side of submucosa (mucosal or serosal) was able to better differentiate PC12 cells. Methods for seeding PC12 cells on both sides of submucosa were similar as described above. It was observed that the mucosal side of submucosa appeared to be more venerable for differentiation of neuronal cells as compared to the other side of submucosa.

To observe the effect of Gamma irradiation on the differentiation of PC1 2 cells, PC12 cells were seeded on both sides of Gamma radiated submucosa. Preliminary results indicate that the degree of differentiation of cells cultured on gamma radiated submucosa was higher than cells cultured on regular submucosa (hydrated ETO, PAA). This study was done only once (n=1) in triplicate, therefore repeated studies are required to confirm the results. However these initial results suggest the possibility of gamma radiation assisting in breaking/disturbing mechanical structure of submucosa and releasing some sort of differentiating promoting factors to show increased differentiation.

To determine the effect of physically moving the culture plate ("Mechanical Disturbance Studies") on cell differentiation, PC12 cells were seeded on submucosa as described above. The seeded culture plate was not moved for 5 days and cells were monitored under the microscope. The experiment was conducted once (n=1) in 6 wells. Physically moving the culture plate resulted in lower degree of differentiation, implying that movement of the culture plate after seeding interferes with cell differentiation.

Two experiments were performed in duplicate to determine the effect of changing the media on cell differentiation. The RPMI media was replaced on 2, 4, 6, 8 and 10 days in the wells which consisted of cells seeded on submucosa mucosal side and submucosa abluminal side, negative control and control, where cells were seeded on uncoated plate without NGF. The experiment was repeated twice (n=2) with triplicates. Results from this study indicated that change in media had no significant effect in cell differentiation using either side of submucosa and negative control. However in the control the cells did not float and die as early as the control cells cultured without a change in the media.

EXAMPLE 4

Antibody Neutralization Studies of PC12 Cells Cultured on Submucosal Tissue Substrates Materials & Methods Cells: Rat Pheochromocytoma (PC12) cells were obtained from American Type Culture Collection (Rockville, Md.) and were cultured as described by Green Tishler (1983). Initially the cells were grown to confluence in monolayers attached to plastic 75 cm flasks. PC12 cells were maintained in RPMI 1640 medium supplemented with 10% horse serum, 5% fetal bovine serum, 1% L-glutamine and 100 units/ml penicillin and 100 ug/ml streptomycin. Passages 3–4 were used for these studies at a concentration of 40,000 cells/ml.

Culture plates: 12-well plates (Falcon) were treated overnight with 1 ml of a solution of 0.2 mg/ml rat tail collagen at 37° C. The collagen coated plates were used for the experiments within 3 days of coating.

Test Media: RPMI Complete media and Submucosal Tissue Conditioned Media (STCM) were used in these experiments. STCM was prepared by incubating serum-free RPMI 1640 stock media with PAA (0.1%) & gamma (1 MRad) treated submucosal tissue at a concentration of 2 g submucosal tissue for each 15 ml of media. Treatment was for 48 hours at 37° C. Serum & other supplements were added to the submucosal tissue treated media to yield the STCM.

Growth Factors: Mouse 7S-NGF (BT-5023) was purchased from Harlan and was utilized at a concentration of 50 ng/ml. Recombinant bovine FGF2 (1363-719) was purchased from Boehringer Mannheim and was used at a concentration of 10 ng/ml.

Antibodies: Anti-mouse NGF (1087-754) was purchased from Boehringer Mannheim and was used at a concentration of 150 ng/ml. Rabbit anti-bovine FGF2 (AB-33-NA) was purchased from R&D and used at a concentration of 40–50 1g/ml.

Method. PC12 cells were plated in duplicate at a concentration of 40,000 cells/ml in 12-well plates containing 0.5 ml of RPMI medium or STCM. Growth factors and/or antibodies were added as appropriate. Cultures were evaluated for PC12 differentiation 48 hours after plating by counting 3–20× fields per well.

Differentiation: PC12 cells were considered differentiated if they exhibited at least one neurite-like extension which extended a minimum of 2 cell body diameters from the cell nucleus.

Results

RPMI Media Treatments: It was discovered that NGF & FGF2 both induced PC12 differentiation in the concentrations tested. Wells not containing growth factor did not differentiate. It was noted that the growth factor activity was effectively neutralized by the addition of the respective neutralizing antibody to the neurite-inducing factor. Addition of anti-NGF to the wells containing FGF2 also blocked differentiation in RPMI 1640 media, addition of anti-FGF2 to the wells containing NGF did not alter differentiation.

STCM Treatments: STCM induced differentiation of PC12 cells. Differentiation was effectively-blocked with the addition of anti-FGF2 neutralizing antibody. Addition of anti-NGF neutralizing antibody had no effect on differentiation.

Conclusions

1. STCM contains a substance that causes PC12 differentiation. The effect of this substance can be neutralized with the addition of anti-FGF2 neutralizing antibody.
2. PC12 differentiation in the STCM is not affected by the addition of anti-NGF neutralizing antibody.
3. The anti-NGF neutralizing antibody may cross react with bovine FGF2. It is also possible that the antibody binds non-specifically to the FGF2 receptor.

EXAMPLE 5

Sciatic Nerve Regeneration

Experimental Design and Surgical Procedure

Small intestinal submucosal graft material, in sheet form, was prepared in accordance with the present invention and sterilized by exposure to 0.1% peracetic acid. A single sheet of submucosal tissue was formed in the shape of a tube having a luminal diameter of about 2 mm and the opposing ends of the sheet tissue were sutured longitudinally along the axis of the tube. The lumen of the submucosal tissue tube was filled with a suspension of comminuted submucosal tissue immediately before implantation of the graft construct into the rat.

Eleven medium sized Sprague-Dawley laboratory rats were anesthetized (Ketamine 90 mg/kg and Xylazine 10 mg/kg, I.M.) and approximately 6 to 7 mm of the tibial branch of the sciatic nerve was resected in each of the rats. The resected portion was replaced with either an empty silastic tube (serving as the control) or a fluidized submucosal tissue filled tube construct. The two severed ends of the tibial branch were inserted into the prepared tubes, one severed nerve end being placed in the first end of the tube and the other severed nerve end inserted into the opposite ends of the tube such that a gap of about 6 to about 7 mm separated the two ends of the resected tibial branch. Five of the rats served as controls, having the severed nerve ends placed within an empty silastic tube, and six rats had the severed nerve ends inserted into submucosal tissue tubes in direct contact with the fluidized submucosal tissue (See Table 2). The graft constructs were fixed in place by suturing to the surrounding tissue. The wound was irrigated with normal saline and closed with staples. Immediately post-operative care included placement on a heating pad, covering with a towel, turning every 15 minutes until awake and moving, and monitoring heart rate and respirations.

The animals were monitored daily, and at 30 days all rats were observed using their legs only to push off. No grasping was recorded. Four animals were sacrificed on Aug. 23, 1997. The two rats having the silastic tube implanted showed some signs of neuronal tissue growth and some directed growth along the tubes axis. However, in the submucosal tissue tube constructs, the resected ends of the tibial branch appeared to have reattached.

TABLE 2

Experimental timetable

| Group | Animal | Submucosal Tissue Tube Constructs | Silastic Tube | Post Dates |
|---|---|---|---|---|
| 30 Days | #1 | 7-23-97 | | 8-23-97 |
| | #2 | 7-24-97 | | |
| | #3 | | 7-24-97 | |
| | #4 | | 7-25-97 | |
| 60 Days | #5 | 7-28-97 | | 9-20-97 |
| | | died 8-4-97 | | |
| | #6 | 7-28-97 | | |
| | #7 | | 7-25-97 | |
| | #8 | | 7-28-97 | |
| 120 Days | #9 | 7-29-97 | | |
| | #10 | 7-29-97 | | 11-17-97 |
| | #11 | | 7-29-97 | |

What is claimed is:

1. A tissue graft construct for promoting the repair of damaged or diseased neurological related tissues in a warm-blooded vertebrate, said construct comprising intestinal submucosal tissue delaminated from both the tunica muscularis and at least the luminal portion of the tunica mucosa of warm-blooded vertebrate intestine, or a digest thereof and an added growth factor.

2. The construct of claim 1, wherein the growth factor is selected from the group consisting of nerve growth factor and fibroblast growth factor.

3. The tissue graft construct of claim 1 wherein the submucosal tissue comprises a tube of submucosal tissue and fluidized submucosal tissue located in the lumen of the tube of submucosal tissue, wherein the fluidized submucosal tissue is selected from the group consisting of comminuted and solubilized submucosal tissue or an extracted fraction thereof.

4. A tissue graft construct for repairing neurological tissues, said composition comprising a biodegradable tube having a luminal diameter sized to receive nerve tissue; and fluidized submucosal tissue selected from the group consisting of comminuted and solubilized submucosal tissue, wherein the fluidized submucosal tissue is located in the lumen of the tube.

5. The tissue graft construct of claim 4 wherein the biodegradable tube comprises submucosal tissue.

6. The tissue graft construct of claim 4 wherein the biodegradable tube has a luminal diameter of about 0.5 mm to about 2 cm.

7. A process of using submucosal tissue of a warm-blooded vertebrate in the manufacture of a tissue graft construct useful for inducing the repair of neurological tissue in a warm-blooded vertebrate, said process comprising the step of combining submucosal tissue of a warm-blooded vertebrate, or a digest thereof, with an added growth factor selected from the group consisting of nerve growth factor and fibroblast growth factor.

8. A process of using submucosal tissue of a warm-blooded vertebrate in the manufacture of a tissue graft construct useful for inducing the repair of neurological tissue in a warm-blooded vertebrate, said process comprising the step of forming a tube of submucosal tissue having a luminal diameter of about 0.5 mm to about 2 cm and introducing into the lumen of said submucosal tissue tube fluidized submucosal tissue selected from the group consisting of comminuted submucosal tissue and solubilized submucosal tissue.

9. The process of claim 8 further comprising the step of sealing at least one end of the tube of submucosal tissue.

10. A method for promoting the repair of damaged or diseased neurological related tissues in a warm-blooded vertebrate, said method comprising the step of contacting the site in need of repair with a composition comprising intestinal submucosal tissue delaminated from both the tunica muscularis and at least the luminal portion of the tunica mucosa of warm-blooded vertebrate intestine.

11. The method of claim 10 wherein the neurological tissue is dura mater.

12. The method of claim 10 wherein the neurological tissue comprises neurons of the central nervous system.

13. The method of claim 10 wherein said submucosal tissue is fluidized.

14. The method of claim 13 wherein said submucosal tissue is injected at the site in need of repair.

15. The method of claim 10 wherein said submucosal tissue is surgically implanted at the site in need of repair.

16. The method of claim 10 wherein said submucosal tissue is in powder form.

17. A method for inducing the formation of neurological related tissue between endogenous neurological tissue structures in a warm blooded vertebrate at a site in need of endogenous neurological related tissue growth, said method comprising surgically implanting a graft composition comprising submucosal tissue of a warm-blooded vertebrate to bridge the endogenous neurological tissue structures to induce endogenous neurological related tissue growth between the bridged neurological structures.

18. The method of claim 17, wherein the graft composition is fluidized and is administered by injection into the warm-blooded vertebrate.

19. The method of claim 17, wherein the graft composition is administered by surgically implanting the composition into the warm-blooded vertebrate.

20. The method of claim 17, wherein the neurological related tissue is dura mater.

21. The method of claim 17 wherein the neurological related tissue comprises neurons of the central nervous system.

22. A tissue graft construct for repairing neurological tissues, said composition comprising a biodegradable tube having a luminal diameter sized to receive nerve tissue;

fluidized submucosal tissue selected from the group consisting of comminuted and solubilized submucosal tissue, wherein the fluidized submucosal tissue is located in the lumen of the tube; and an added growth factor.

23. A method of manufacturing a submucosal tissue graft construct useful for inducing the repair of neurological tissue in a warm-blooded vertebrate, said manufacture comprising the steps of:

forming a tube of submucosal tissue having a luminal diameter of about 0.5 mm to about 2 cm and introducing into the lumen of said submucosal tissue tube fluidized submucosal tissue selected from the group consisting of comminuted submucosal tissue and solubilized submucosal tissue; and adding, an exogenous growth factor to the graft construct.

* * * * *